(12) United States Patent
Teicher et al.

(10) Patent No.: US 7,942,828 B2
(45) Date of Patent: *May 17, 2011

(54) METHOD FOR DETERMINING FLUCTUATION IN ATTENTIONAL STATE AND OVERALL ATTENTIONAL STATE

(75) Inventors: Martin H. Teicher, Rye, NH (US); Steven B. Lowen, Burlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/771,036

(22) Filed: Feb. 3, 2004

(65) Prior Publication Data

US 2004/0220493 A1 Nov. 4, 2004

Related U.S. Application Data

(63) Continuation-in-part of application No. 09/860,701, filed on May 17, 2001, now Pat. No. 6,685,652.

(60) Provisional application No. 60/204,663, filed on May 17, 2000, now abandoned.

(51) Int. Cl.
*A61B 5/00* (2006.01)

(52) U.S. Cl. ........................... 600/558; 600/559

(58) Field of Classification Search ........... 600/558–559
See application file for complete search history.

(56) References Cited

U.S. PATENT DOCUMENTS

| | | | |
|---|---|---|---|
| 4,770,636 A | 9/1988 | Buschke | 434/236 |
| 4,889,422 A * | 12/1989 | Pavlidis | 351/210 |
| 5,142,590 A | 8/1992 | Carpenter et al. | 382/14 |
| 5,377,100 A | 12/1994 | Pope et al. | 364/410 |
| 5,511,982 A * | 4/1996 | Pigache et al. | 434/350 |
| 5,724,987 A * | 3/1998 | Gevins et al. | 600/544 |
| 5,771,261 A * | 6/1998 | Anbar | 374/45 |
| 5,795,155 A | 8/1998 | Morrel-Samuels | 434/107 |
| 5,801,810 A * | 9/1998 | Roenker | 351/246 |
| 5,888,074 A * | 3/1999 | Staplin et al. | 434/258 |
| 5,913,310 A * | 6/1999 | Brown | 128/897 |
| 5,940,801 A * | 8/1999 | Brown | 705/2 |
| 5,983,129 A | 11/1999 | Cowan et al. | 600/544 |
| 6,053,739 A * | 4/2000 | Stewart et al. | 434/236 |

(Continued)

FOREIGN PATENT DOCUMENTS

| | | |
|---|---|---|
| WO | WO 01/87142 | 11/2001 |
| WO | WO 03/073212 | 9/2003 |

OTHER PUBLICATIONS

Arve et al. "Auditory attentional shifts in reading-disabled students: quantification of attentional effectiveness by the attentional shift index," 1998, Neuropsychologia, vol. 36, No. 2, pp. 143-148.*

(Continued)

*Primary Examiner* — Max Hindenburg
*Assistant Examiner* — Rene Towa
(74) *Attorney, Agent, or Firm* — Clark & Elbing LLP

(57) ABSTRACT

The invention provides methods for determining shifts in the attentional state of a subject. These methods are useful for diagnosing subjects with a psychological or behavioral disorder. The invention also features methods for determining the effect of a therapy on the overall attentional state and shifts in the attentional state of a subject.

100 Claims, 6 Drawing Sheets

| MEASURES | ADHD | NL | F(1,66) = | p < | EFFECT SIZE |
|---|---|---|---|---|---|
| Standard CPT Parameters | | | | | |
| Errors of Commision | 27.9 ± 2.4 | 11.6 ± 6.6 | 5.38 | 0.03 | 0.89 |
| Errors of Omission | 13.1 ± 1.8 | 1.2 ± 4.9 | 5.20 | 0.03 | 0.87 |
| Latency | 537 ± 101 | 619 ± 28 | 7.68 | 0.007 | 1.06 |
| Variability (S.D.) | 179 ± 7.2 | 134 ± 20 | 4.82 | 0.03 | 0.84 |
| Attention Shift Analysis | | | | | |
| Time on Task (%) | 42.6 ± 3.8 | 82.4 ± 10.4 | 12.95 | 0.0006 | 1.37 |
| Shifts (#) | 12.8 ± 0.6 | 5.4 ± 1.6 | 19.22 | 0.00004 | 1.67 |

U.S. PATENT DOCUMENTS

| | | | | |
|---|---|---|---|---|
| 6,102,873 | A * | 8/2000 | Claessens | 600/595 |
| 6,113,538 | A * | 9/2000 | Bowles et al. | 600/300 |
| 6,241,686 | B1 | 6/2001 | Balkin et al. | 600/544 |
| 6,496,724 | B1 * | 12/2002 | Levendowski et al. | 600/544 |
| 6,625,485 | B2 * | 9/2003 | Levendowski et al. | 600/544 |
| 6,753,782 | B2 * | 6/2004 | Power | 340/573.4 |
| 6,898,455 | B2 * | 5/2005 | Anderson et al. | 600/411 |

OTHER PUBLICATIONS

Greenberg, "An objective measure of methylphenidate response: clinical use of the MCA," Psychopharmacology Bulletin 23:279-282 (1987).

Rosvold et al., "A continuous performance test of brain damage," Journal of Consulting and Clinical Psychology 20:343-350 (1956).

Teicher et al., "Objective Measurement of Hyperactivity and Attentional Problems in ADHD," J. Am. Acad. Child Adolesc. Psych., 35:334-342 (1996).

Mark Strecker, "Objective Testing for Attention Disorders," *The Institute for Family Development* pp. 1-4.

Teicher et al., "Objective Measurement of Hyperactivity and Attentional Problems in ADHD," *J. Am. Acad. Child Adolesc. Psych*. 35:334-342 (1996).

* cited by examiner

Figure 1

| MEASURES | ADHD | NL | F(1,66) = | p < | EFFECT SIZE |
|---|---|---|---|---|---|
| Standard CPT Parameters | | | | | |
| Errors of Commision | 27.9 ± 2.4 | 11.6 ± 6.6 | 5.38 | 0.03 | 0.89 |
| Errors of Omission | 13.1 ± 1.8 | 1.2 ± 4.9 | 5.20 | 0.03 | 0.87 |
| Latency | 537 ± 101 | 619 ± 28 | 7.68 | 0.007 | 1.06 |
| Variability (S.D.) | 179 ± 7.2 | 134 ± 20 | 4.82 | 0.03 | 0.84 |
| Attention Shift Analysis | | | | | |
| Time on Task (%) | 42.6 ± 3.8 | 82.4 ± 10.4 | 12.95 | 0.0006 | 1.37 |
| Shifts (#) | 12.8 ± 0.6 | 5.4 ± 1.6 | 19.22 | 0.00004 | 1.67 |

US 7,942,828 B2

METHOD FOR DETERMINING FLUCTUATION IN ATTENTIONAL STATE AND OVERALL ATTENTIONAL STATE

CROSS REFERENCE TO RELATED APPLICATIONS

This application is a continuation-in part and claims priority to U.S. Ser. No. 09/860,701, filed May 17, 2001, now U.S. Pat. No. 6,685,652, and U.S. Ser. No. 60/204,663, filed May 17, 2000, abandoned, both of which are incorporated herein by reference.

BACKGROUND OF THE INVENTION

A subject's visual attention can be tested by displaying a series of visual stimuli, to which the subject is instructed to respond. Typically, the stimuli are of two types, and the subject is instructed to respond to only one of them. Data are collected for each stimulus presented including the type of stimulus, whether or not the subject responded, and if so, how long the subject took to respond. The continuous performance attention task has been in use since the mid 50's (Rosvold et al., 1956, J. of Consulting and Clinical Psychology, 20: 343-350), with computerized versions available in the 1970's (Greenberg, 1987, 23: 279-282). The previous methods of analysis of the raw data generated from these methods have typically distilled the data into a few numbers which do not capture the subject's fluctuations in attention.

Another method for assessing the visual attention capabilities of a subject involves determining how long a particular visual stimulus must be present before a subject can detect it (U.S. Pat. No. 5,801,810). This method does not reveal the attentional state of the subject, rather, it requires the subject to be fully attentive.

Other reported methods determine a subject's intensity of focused attention, concentration, and/or interest by measuring signals naturally emanating from the brain (U.S. Pat. Nos. 5,983,129 and 5,377,100). These brainwaves vary across subjects and even within the same subject; thus, these methods do not provide a reliable, well-defined number for classifying attentional states.

A diagnostic assessment of psychological conditions can be made by conducting a sequence of continuous performance tasks where information is recorded to reflect the number of target stimuli correctly identified, the number of target stimuli missed, the number of responses to non-target stimuli, the number of non-target stimuli correctly missed, and the final interstimulus interval (U.S. Pat. No. 5,940,801). This method can be used in a clinical setting, as well as remote locations such as the home, school, or workplace. Using this method in remote locations is useful for psychological and behavioral problems that are highly stimulus-dependent and may not be manifested in a clinical environment, such as depression, anxiety, schizophrenia, addiction, eating disorders, attention deficit disorders, attention deficit and hyperactivity disorder. This method does not provide a way to classify performance into states.

The aforementioned methods do not accurately quantify a subject's attentional state. None classify a subject's behavior into specific well-defined states or examine fluctuations in attention over time.

SUMMARY OF THE INVENTION

In one aspect, the invention features a method of acquiring information about the attentional state of a subject. The method involves (a) presenting to the subject a sequence of a predetermined number of stimuli over a predetermined period of time, wherein the sequence includes target and nontarget stimuli, (b) scoring the response of the subject on the percentage of targets responded to and the percentage of nontargets responded to, and (c) on the basis of the scoring of step (b), making a determination of the attentional state of the subject.

This method can be used to assess both overall attention and impulsivity. This method can be repeated three or more times to determine the pattern of attentional states and the time spent in each state.

This method can be used to diagnose the subject being tested for a psychological, neurological, or behavioral disorder, such as depression, an anxiety disorder, schizophrenia, a drug addiction, an eating disorder, an attention deficit disorder, an attention deficit and hyperactivity disorder, a learning disorder, or Alzheimer's disease, dementia, epilepsy, stroke or traumatic brain injury. This method can be used to identify a subject at risk for a psychological, neurological, or behavioral disorder or to diagnose a subject with such a disorder. Additionally, this method can be used to determine the preferred therapy for the treatment of a psychological, neurological, or behavioral disorder or to correlate the attention state of a subject involved in a clinical trial of a therapy for a psychological or behavioral disorder with the success or failure of the therapy to improve the subject's condition.

This method can also be used to assess the eligibility of a subject to obtain a driver's license or a volunteer or paid position, including those that require a longer than average attention span, such as, an air traffic controller, pilot, emergency room doctor, surgeon, police officer, military officer, or fire-fighter.

In a related aspect, the invention features a method of determining whether a therapy affects the attentional state of a subject. This method involves (a) presenting to the subject undergoing treatment with the therapy a sequence of a predetermined number of stimuli over a predetermined period of time, wherein the sequence comprises target and nontarget stimuli, (b) scoring the response of the subject on the percentage of targets responded to and the percentage of nontargets responded to, and (c) on the basis of the scoring of step (b), making a determination of the attentional state of the subject. An altered attentional state, compared to either the attentional state of the subject when not undergoing treatment with the therapy or the attentional state of a control subject when not undergoing treatment with the therapy, indicates that the therapy affects the attentional state of the subject.

In one embodiment of this aspect, both overall attention and impulsivity are assessed. This method may be repeated three or more times to determine the pattern of attentional states and the time spent in each state. This method may also further include comparing the effect of the therapy on the attentional state of the subject to the effect of another therapy on the attentional state of the subject. Additionally, this method may further involve comparing the attentional state of a subject diagnosed with a disorder to that of a subject not diagnosed with the disorder.

In various embodiments, the subject is diagnosed with a psychological or behavioral disorder, such depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury. In other embodiments, the subject is involved in a clinical trial of a therapy for a psychological, neurological, or behavioral disorder. This method may be also used to determine the preferred therapy for the treatment of a psychological, neurological, or behavioral disorder.

In one desirable embodiment of any of the methods of the invention, the stimuli are visual symbols or audio sounds. The symbols can be individual numbers, letters, or shapes, or a combination of the above. Preferably, the stimuli are presented using a computer screen or speaker and the subject's responses are recorded using a computer. In another desirable embodiment of the invention, the stimuli number 15, 20, 30, or greater within each analysis period. The test may be conducted in a clinical setting or across a network.

BRIEF DESCRIPTION OF THE DRAWINGS

FIG. 1 is a table showing the assessment of the attentional state of children diagnosed with attention deficit hyperactivity disorder ("ADHD") and the attentional state of normal children not diagnosed with ADHD ("NL") using traditional continuous performance task (CPT) parameters and using the method of the present invention.

DETAILED DESCRIPTION

Figure 2:
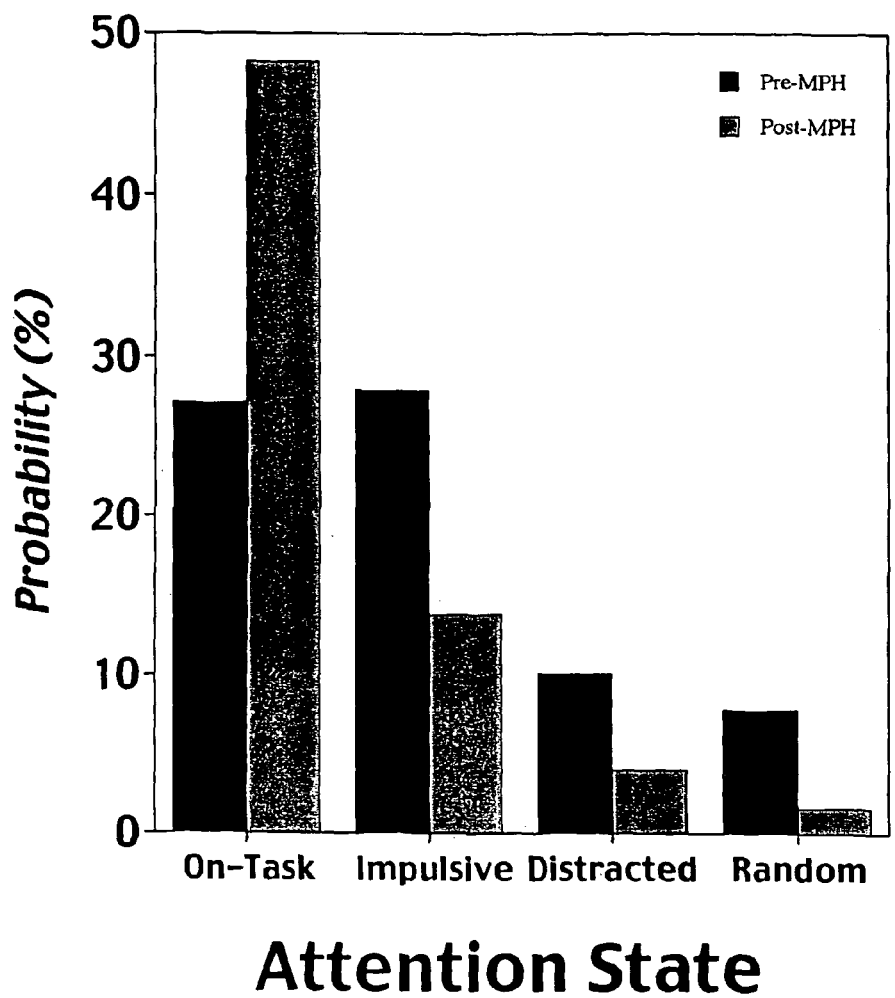
FIG. 2 is a bar graph of the probability of entering into one attentional state (i.e., "On Task," "Impulsive," "Distracted," or "Random" state) from any other attentional state based on 989 state entries in the premedicated state and 513 state entries after treatment with methylphenidate.

The invention features a method of assessing the attentional sate of a subject and measuring the fluctuations in the attentional state of the subject. This method determines both the implusivity and overall attention of the subject and classifies the subject's attentional state accordingly. The invention also includes the novel method of determining and classifying the types and time course of fluctuations in attention state. Additionally, the invention includes a novel method of determining the effect of a therapy on the attentional state of a subject. The invention gives greater insight into the nature of the attentional process than prior methods which summarize the entire session or larger segments of the session into a set of measures.

This simple and rapid method of classifying behavior involves presenting a subject with a sequence of a predetermined number of stimuli over a predetermined period of time. These stimuli can be visual symbols or audio sounds, and they can be presented to the subject using a computer. The response of the subject is scored based on the percentage of target stimuli responded to and the percentage of nontarget stimuli responded to.

The following examples are to illustrate the invention; they are not meant to limit the invention in any way.

Assessment of Attentional State During a Computerized Task

A sequence of 15 stimuli are presented sequentially at two second intervals, over a total duration of 30 seconds. Each of the stimuli is either a target or a non-target stimulus, chosen randomly with equal probability, and chosen independently of the other stimuli. Although the total number of symbols remains fixed at 15, the numbers of target and non-target symbols vary, but generally do not differ by more than about 5. The percentage of targets to which the subject responds is calculated, and denoted T. Similarly, the percentage of responses to non-targets is denoted N.

If a subject does not discriminate between targets and non-targets, then the two percentages T and N will be similar. A subject is defined to be "Randomly" responding if N and T differ by less than 25%, and the subject responds to most of the stimuli. Conversely, a subject is "Minimally responding" if N and T agree within 25% but the subject responds to less than half of the stimuli.

For a perfect response, T is 100%, and N is 0%. A subject is defined to be "On Task" if T is 85% or greater, and N is 20% or less. An impulsive subject typically responds to target stimuli with good accuracy, but exhibits errors of commission. If T is 85% or greater and N exceeds 20% (and the subject is not Randomly responding), then the subject is defined to be "Impulsive." A subject who misses more than 15% of the target stimuli (T is less than 85%), responds to a greater percentage of target than non-target stimuli (T is greater than N) and is not Randomly or Minimally responding, is defined as "Distracted."

Finally, a subject could respond to more non-target than target stimuli, either intentionally or through confusion. If N exceeds T by more than 25%, then the subject is defined to be "Contrary."

The above procedure is repeated using additional blocks of symbols of the same length. Thus, the attention state can be recorded after each block and used to determine the amount of time spent in each state, the pattern of attention states, and the range of attention states occupied by the subject.

Comparison of the Fluctuations in Attentional State of Subjects Diagnosed with Attention Deficit Hyperactivity Disorder to that of Normal Subjects The attentional state of subjects diagnosed with attention deficit hyperactivity disorder (ADHD) and the attentional state of normal subjects were measured using a computer-driven vigilance task coupled to a high precision motion analysis system. The vigilance task required subjects to respond to the presentation of eight pointed stars and to withhold response to five pointed starts. These symbols were presented at random screen positions every other second for a period of 200 milliseconds (450 stimuli per test with a 50% probability of the target stimuli). The accuracy and response latency to each stimulus was recorded. For each successive 30 second segment, the response was divided into "On Task," "Impulsive," "Distracted," "Random Responding," "Minimal Responding," and "Contrary Responding" attentional states, based on the percent responses to targets and non-targets using the criteria described above.

To assess the effects of racemic methylphenidate (MPH, also called Ritalin) on attention, 60 boys (10.1±1.3 years of age) with ADHD (DSM-IV combined subtype based on standard diagnostic methods using K-SADS-E, which is the children's version of the schedule for affective disorders and schizophrenia) were studied off all medication. These children had previously taken MPH as their only treatment but had not taken MPH for at least 24 hours prior to this study. Thus, these children had an undetectable level of MPH in their bloodstream. The children were also retested 120 minutes after administration of a probe-dose of MPH (0.4 mg/kg PO). Comparisons were made to a new group of eight healthy normal male controls (11.3±2.0 years of age; p>0.2) without ADHD (based on an assessment using the K-SADS-E criteria) (FIG. 1).

On average, unmedicated children with ADHD had 12.8 shifts between different attention states compared to only 5.4 shifts in controls (F[1,66]=19.2, p<0.0001). Following treatment with MPH, the attentional state of the children with ADHD shifted only 7.0 times per test (F[1,59]=67.7, p<10-10), which was not significantly different than the number of times the control children without ADHD changed attentional states (p>0.4). Prior to treatment with MPH, children with ADHD were "On Task" during only 42.6% of the 30 second epochs vs. an 82.4% "On Task" rate for control children (F[1,66]=12.9, p<0.001). After treatment with MPH, the "On Task" rate increased to 75.4% ($p<10^{-11}$). As shown in FIG. 1, the number of shifts in attention state ("Shifts" row) and the percent of attention states that satisfied the "On Task" criteria ("Time on Task" row) were more robust indicators of the differences between ADHD children and normal controls ("NL" column) than traditional continuous performance task (CPT) parameters.

MPH markedly increased the likelihood that children with ADHD would persist in an "On Task" state (Chi squared, $p<10^{-20}$) and attenuated their proclivity to persist in a "Distracted" state (Chi squared, p<0.003). MPH did not significantly affect the probability that they would persist in an "Impulsive" or "Random" response state (both p>0.2). However, MPH significantly attenuated their proclivity to enter into an "Impulsive" or "Random" states from another attentional state (both $p<10^{-15}$; FIG. 2). These results illustrate the ability of the methods of the present invention to determine the effect of a therapy on the attentional state of a subject.

The following example is meant to illustrate the invention. It is not meant to limit the invention in any way.

EXAMPLE

Methods

Subjects

For this IRB-approved study, children were recruited via the regional newspaper advertisement for a study of either healthy controls or hyperactive boys ages 9 to 12 medicated with short-acting stimulants. The study was conducted within a clinical research program at a university-affiliated, major psychiatric hospital located in a suburban city. Parent(s) provided written informed consent, and each child gave verbal assent. To enter the study, children needed to meet the Diagnostic and Statistical Manual of Mental Disorders, 4th Edition criteria for ADHD-Combined Type (APA 1994) assessed by means of structured parent/child interviews using the Schedule for Affective Disorder and Schizophrenia for School-Age Children, Epidemiologic Version, Fifth Revision (Orvaschel and Puig-Antich 1994). The children could not have current major mood disorder, psychosis, tic disorder, a major anxiety disorder or metal retardation. Children with oppositional defiant disorder or reported learning disorders could participate. Control children could not meet criteria for any Axis-1 DSM-IV diagnosis. The sample consisted of a control group of 8 boys who averaged 11.3±2.0 (S.D.) years of age, and an ADHD group of 60 boys with a mean age of 10.6±1.1 years ($F_{1,66}$=1.8, p=0.18). Of the 60 ADHD boys, 19 had comorbid Oppositional Defiant Disorder; 2 had current Dysthymia; 4 had previously diagnosed Learning Disorders; 3 had past Major Depression or past Anxiety Disorders. The ADHD children had an average Abbreviated Conners Hyperactivity Index (Goyette et al., J. Abnorm. Child Psychol. 6:221-236, 1978) score of 19 (any score over 15 is indicative of hyperactivity). Their average Achenbach Child Behavior Checklist (Achenbach. Diagnostic and Statistical Manual of Mental Disorders, $4^{th}$ ed., 1991) Internalizing Problem Score was 20, average Externalizing Problem Score was 29, with a Total Problem Score of 49.

Study Design

Measures were obtained during a single visit. Children with ADHD were assessed at least 18 hours following their last dose of stimulant. Procedures for all subjects included: (1) structured diagnostic interview with K-SADS-E (Orvaschel and Puig-Antich, Schedule for Affective Disorder and Schizophrenia for School-Age Children, Epidemiologic Version, Fifth Revision. Fort Lauderdale, Fla., Nova Southeastern University, 1994); (2) parent ratings; and (3) laboratory assessment using 15-minute computerized attention task and infrared camera motion analysis (Teicher, Harvard Rev. Psychiatry 3:18-35, 1995; Teicher et al., J. Am. Acad. Child Adolesc. Psychiatry 35:334-342, 1996). Following this, boys diagnosed with ADHD received a single dose of MPH (0.4 mg/kg body weight). They were retested 120 minutes later.

Equipment

CPT with Infrared Motion Analysis. Attention and activity were measured using a computer-driven fifteen-minute vigilance task coupled to a high precision motionanalysis system (Teicher, 1995, supra; Teicher et al., 1996, supra; M-MAT, McLean Hospital, Belmont Mass. 02478). The vigilance task required the child to respond by pressing the space bar on a computer to the presentation of 8-pointed stars, but to withhold response to 5-pointed starts. Stars were presented at random screen positions, every other second, for a period of 200 milliseconds each. Concurrently, an infrared motion analysis system tracked and recorded the vertical and horizontal position of a reflective marker (worn on a headband) 50 times per second to a resolution of 0.04 mm. Head movements were analyzed for number of position changes greater than 1.0 mm, called microevents and for total displacement (Teicher, 1995 supra; Teicher et al., 1996, supra). For example, a subject moving their head 50 cm to the left and 50 cm to the right over a 1-second period would produce 50 microevents and a total displacement of 100 cm. The motion analysis system captures the entire movement pattern of the marker with great fidelity, and laboratory assessment of motion with this system has been shown to correlate well with teacher ratings of hyperactivity (Teicher et al., 1996, supra).

Measures

Figure 3:
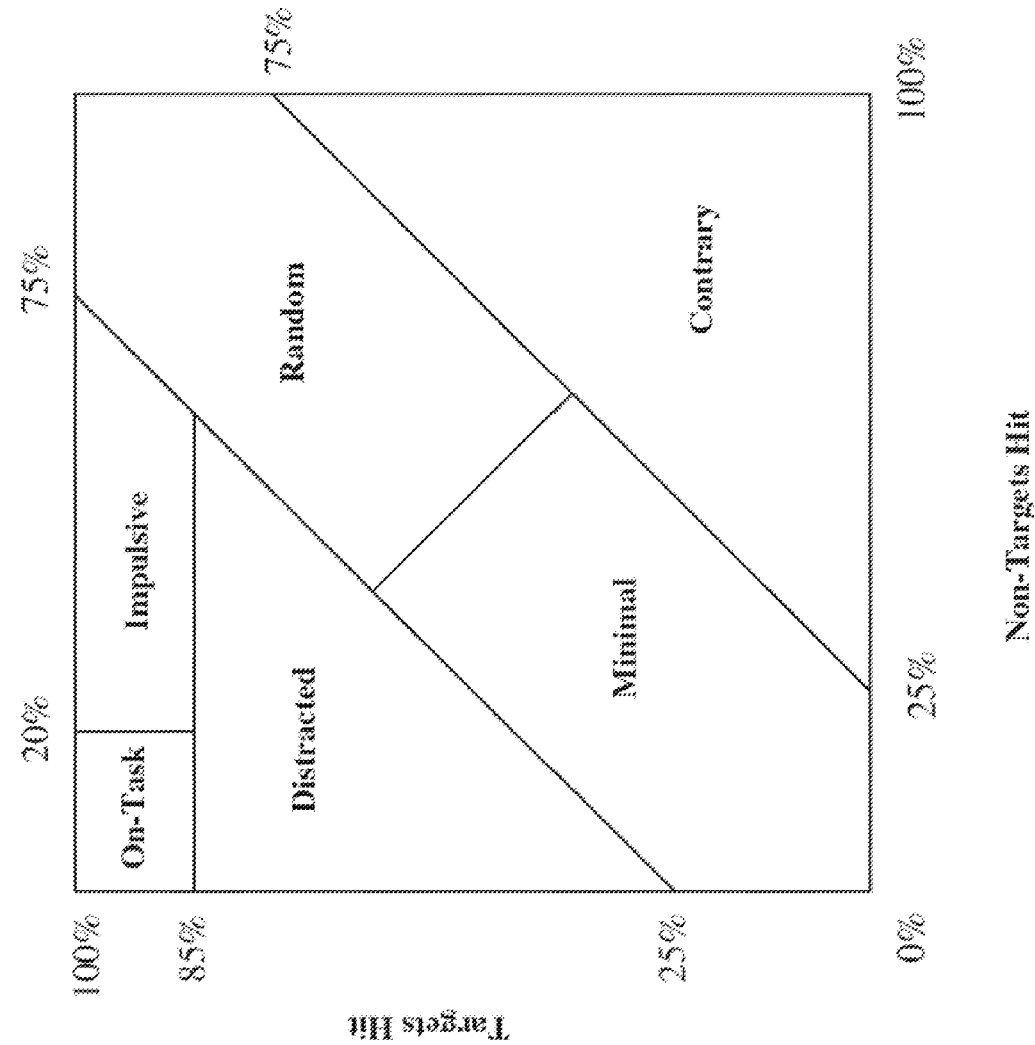
FIG. 3 is a schematic showing the criteria for classifying response into discrete attentional performance states based on percent correct response to targets and non-targets over a 30-second epoch.

The traditional CPT results included errors of commission, errors of omission, and mean correct reaction time with standard deviation. More sophisticated CPT measures, derived from signal detection theory included stimulus sensitivity (d')

and response bias (β) (Nuechterlein, J. Abnorm. Psychol. 92:4-28, 1983). Our novel state measures were derived by dividing the test into 30-second segments, each of which contained 15 stimuli, and each stimulus independently had a 50% probability of being a target. Response to these stimuli was classified by computer into predefined attention response states, based on the percent responses to targets and non-targets (FIG. 3). Initial criteria divided response into one of the following: on-task (high accuracy with few if any errors of omission or commission); impulsive (accuracy better than chance with a significant number of commission errors but few omission errors); distracted (accuracy better than chance with a significant number of omission errors); random (accuracy no better than chance with high level of response to both targets and non-targets); minimal (accuracy no better than chance with low level of responses to either targets or non-targets); and contrary (accuracy significantly worse than chance). However, ADHD children spent very little time in marginal or contrary response states (1.2% and 0.6%, respectively), so these states were pooled into the random response state. For technical reasons attention state measures were not calculated during two 30-second segments because an early software prototype stored the collected movement data at 5 minute intervals, and inadvertently reduced the time period that the computer waited for a key press for the 150th and 300th stimulus.

Statistical Analyses

Between group differences were assessed using independent group ANOVA (SYSTAT, www.spssscience.com/SYSTAT/). Effects of MPH in subjects with ADHD were assessed using repeated measures ANOVA. Post-hoc differences were evaluated using Tukey's tests. Effects of MPH on the conditional probability of persisting in or entering into a specific attentional performance state was evaluated using repeated measures ANOVA. The probability of persisting in each state or switching between each state was calculated for each subject. In some instances probability values were indeterminate (e.g., the probability of persisting in a distracted state for a subject who never entered into the distracted state). Subjects were eliminated from statistical comparison if they had an indeterminate probability of persisting in a given state both off and on MPH. For subjects who had one determinate probability and one indeterminate probability on and off medication, the indeterminate instance was assigned a value of 0, as it can be argued that there was zero probability of persisting in a given state if the state was never entered. (Hence, a subject who had a 0.4 probability of persisting in a distracted state off medication, and had no periods of distraction on medication would be included in the analysis with a 0.0 probability of persistence in the distracted state on medication). Statistical analysis of the effects of methylphenidate on the probability of switching from state A to state B was limited to subjects who had entered state A under both medicated and unmedicated conditions. This is because there is, by definition, a 100% probability that a subject will either persist in a state or switch to one of the alternative states. Although we can assume for statistical purposes that it is unlikely that a subject would persist in a state that they never entered, we cannot assign probabilities to the alternative choices. Correlations between different CPT measures, or between CPT and activity measures were calculated using Pearson's Product Moment correlation. Two-tailed significance tests were used for all comparisons. Values are expressed as mean±standard deviation.

Results

ADHD vs. Control Comparison

Counts of the number of shift changes, and calculations of the percentage of time spent in each state were compared. Unmedicated children with ADHD had 12.8±4.3 attention shifts between attention response states compared to only 5.4±5.7 shifts in controls (F1,66=19.2, p=0.00004). Children with ADHD were "On-Task" during only 42.6±30.3% of the 30 second epochs compared to an 82.4±20.4% "On-Task" rate for normal controls ($F_{1,66}$=12.9, p=0.0006). As shown in Table 1, the frequency of attention shift and percent time on-task measures revealed more robust differences (greater effect sizes) between children with ADHD and healthy controls than did traditional CPT measures. The frequency of attention shifts measure was even associated with a greater effect size differential between ADHD and controls than signal detection theory measures of d' and β.

TABLE I

Differences between children with ADHD and healthy controls (NL) on CPT measures.

| MEASURES | ADHD | NL | F (1, 66)= | p< | EFFECT SIZE |
|---|---|---|---|---|---|
| Standard CPT Parameters | | | | | |
| Errors of Commision | 27.9 ± 19.5 | 11.6 ± 7.9 | 5.38 | 0.03 | 0.89 |
| Errors of Omission | 13.1 ± 14.7 | 1.2 ± 1.3 | 5.20 | 0.03 | 0.87 |
| Latency | 537 ± 77 | 619 ± 88 | 7.68 | 0.007 | 1.06 |
| Variability (S.D.) | 179 ± 58 | 134 ± 27 | 4.82 | 0.03 | 0.84 |
| Signal Detection Theory | | | | | |
| Sensitivity (d') | 1.77 ± 1.63 | 4.02 ± 1.32 | 13.97 | 0.0004 | 1.43 |
| Response bias (β) | 0.64 ± 0.39 | 0.16 ± 0.15 | 11.96 | 0.001 | 1.32 |
| Attention Shift Analysis | | | | | |
| Attention Shifts (#) | 12.8 ± 4.3 | 5.4 ± 5.7 | 19.22 | 0.00004 | 1.67 |
| Time on Task (%) | 42.6 ± 30.3 | 82.4 ± 20.4 | 12.95 | 0.0006 | 1.37 |
| % Time Impulsive | 32.7 ± 18.8 | 14.8 ± 18.5 | 6.45 | 0.02 | 0.97 |
| % Time Distracted | 11.0 ± 13.1 | 1.9 ± 2.8 | 3.89 | 0.06 | 0.75 |
| % Time Random | 13.6 ± 21.7 | 0.9 ± 1.7 | 2.72 | 0.10 | 0.63 |

Pre and Post Medication Comparison

Following MPH attention shifted only 7.0±5.0 times per test ($F_{1,59}$=67.7, $p<10^{-10}$), a rate not significantly different than normal ($F_{1,66}$=0.62, p>0.4). Percent time "On-Task" increased from 42.6±30.3% of the epochs to 75.4±26.3% on MPH ($F_{1,59}$=88.5, $p<10^{-12}$), a level comparable to normal controls ($F_{1,66}$=0.53, p>0.4). As shown in Table 2 the frequency of attention shifts and percent time on-task measures indicated a somewhat greater effect size for MPH treatment than traditional CPT measures.

TABLE 2

Effects of probe-dose methylphenidate (MPH) on CPT performance.

| MEASURES | ADHD | NL | F (1, 66)= | p< | EFFECT SIZE |
|---|---|---|---|---|---|
| Standard CPT Parameters | | | | | |
| Errors of Commision | 27.9 ± 19.5 | 13.6 ± 15.9 | 53.70 | 8.00E−10 | 1.91 |
| Errors of Omission | 13.1 ± 14.7 | 5.0 ± 14.9 | 18.20 | 0.00007 | 1.11 |
| Latency | 537 ± 77 | 500 ± 69 | 24.10 | 8.00E−06 | 1.28 |
| Variability (S.D.) | 179 ± 58 | 123 ± 50 | 64.80 | 5.00E−11 | 2.10 |
| Signal Detection Theory | | | | | |
| Sensitivity (d') | 1.77 ± 1.63 | 3.72 ± 2.00 | 72.92 | 7.00E−12 | 2.22 |
| Response bias (β) | 0.64 ± 0.39 | 0.28 ± 0.30 | 62.38 | 8.00E−11 | 2.06 |
| Attention Shift Analysis | | | | | |
| Attention Shifts (#) | 12.8 ± 4.3 | 7.0 ± 5.5 | 67.70 | 2.00E−11 | 2.14 |
| Time on Task (%) | 42.6 ± 30.3 | 75.4 ± 26.3 | 88.50 | 2.00E−13 | 2.45 |
| % Time Impulsive | 32.7 ± 18.8 | 18.1 ± 17.2 | 29.48 | 1.00E−06 | 1.41 |
| % Time Distracted | 11.0 ± 13.1 | 2.3 ± 4.0 | 31.78 | 5.00E−07 | 1.47 |
| % Time Random | 13.6 ± 21.7 | 4.2 ± 14.6 | 15.52 | 2.00E−04 | 1.03 |

Figure 4:
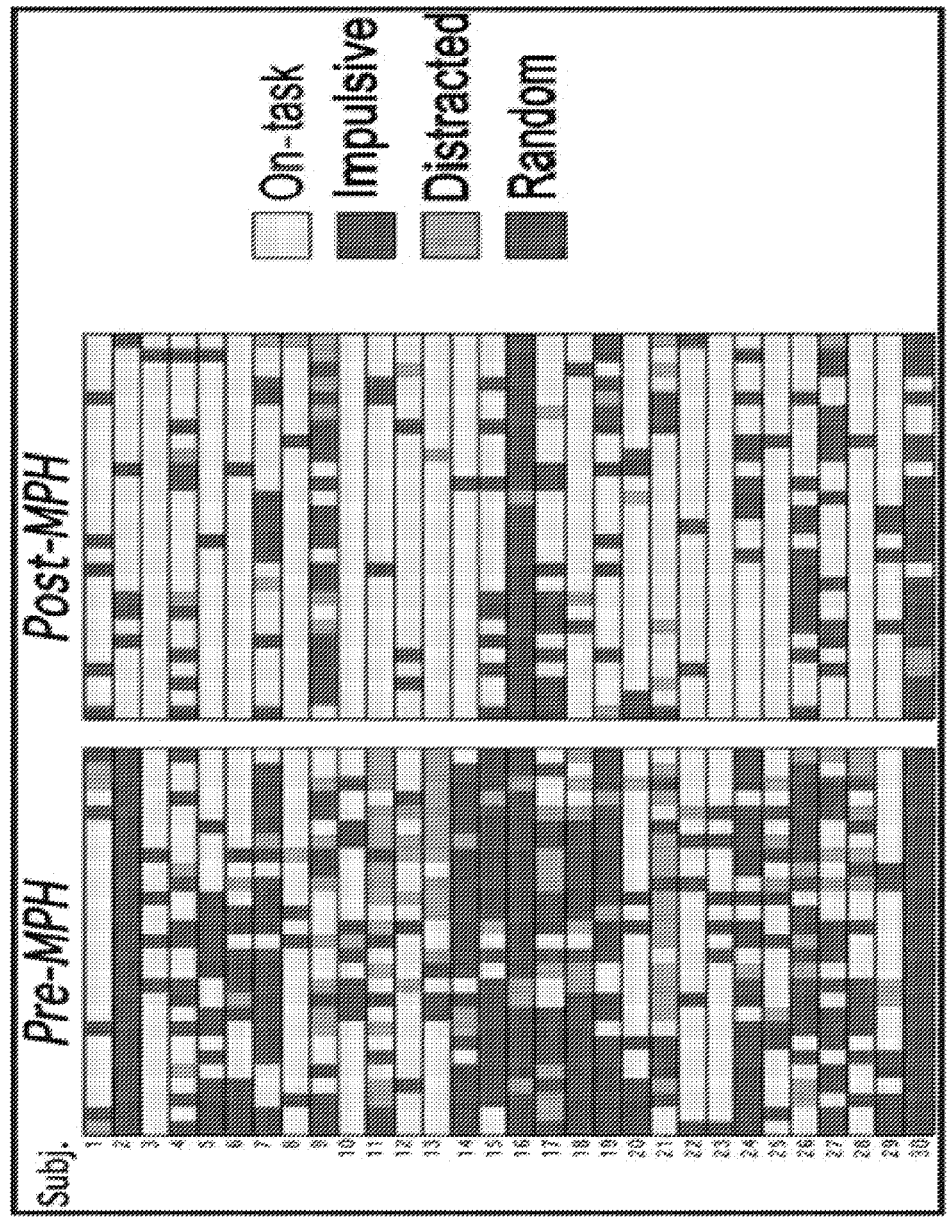
FIG. 4 is a diagram illustrating the pattern of shifts in attentional performance state for the first thirty subjects with ADHD tested prior to and following probe-dose treatment with methylphenidate.

FIG. 4 provides a coded composite of attention state shifts throughout the 15-minute test for the first thirty children with ADHD studied prior to and following treatment with MPH. From this image it is apparent that ADHD children experience many more shifts in attention state, and spend much less time on-task, prior to treatment. It is also apparent that there were marked differences between ADHD children in their attention state profiles.

MPH produced a 77% increase in the percent of time that children with ADHD spent on-task. This was due to marked reduction in the percent time spent in the three states of inattention. Percent time spent in a distracted state of inattention was reduced by 79.3% ($F_{1,59}$=31.8, $p<10^{-6}$). Similarly, MPH produced a 44.5% reduction in time spent in impulsive states ($F_{1,59}$=29.5, $p<10^{-6}$), and a 69.2% reduction in the random response states ($F_{1,59}$=15.5, p=0.0002).

Conditional Probabilities

Figure 5:
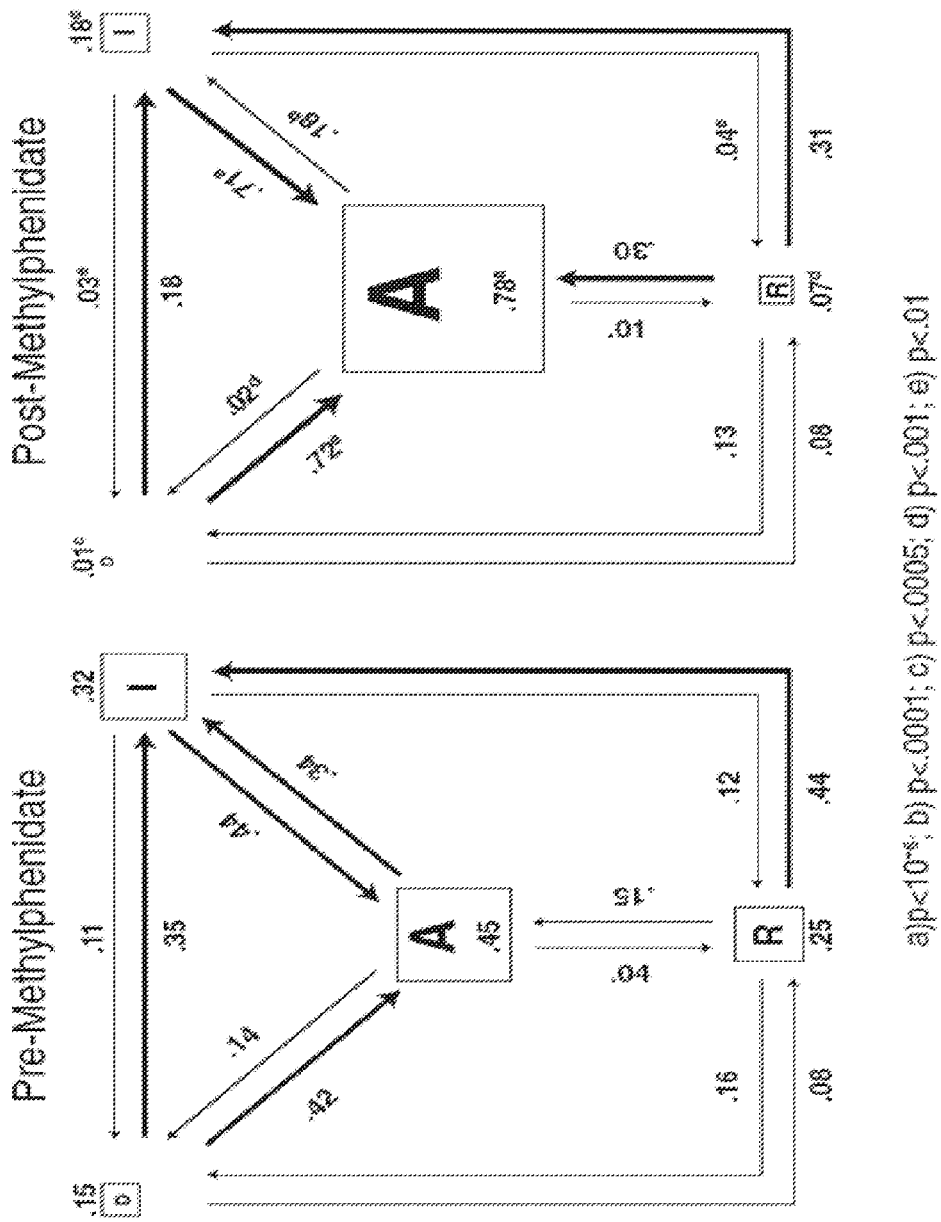
FIG. 5 is a flow chart diagram showing the probability that subjects with ADHD would persist in an attention performance state or shift to one of the other states prior to and following treatment with methyphenidate. Boxes around letters are proportional in size to the probability of persisting in the state. Thickness of arrows is proportion to the probability of shifting from one state to another. Probabilities are indicated as decimal numbers. Abbreviations: A—on-task state; D—distracted; I—impulsive; R—random.

Medications can improve attention by reducing time spent in the distracted, impulsive, and random response states in two different ways. MPH can either reduce the likelihood that a subject will persist in an inattentive response state from one period to the next, or reduce the probability that he will enter a specific inattentive state from another state. FIG. 5 provides pre- and post-medication flow diagrams indicating the overall probability that ADHD subjects would persist in a given state or the probability that they would shift from that state to one of the alternative states.

Methylphenidate produced a 93% reduction in the probability that ADHD children would persist in the distracted state ($F_{1,45}$=15.5, p=0.0003). Methylphenidate also reduced by 70% the probability of persisting in the random response state ($F_{1,37}$=13.6, p=0.0007), and reduced by 42% the probability of persisting in the impulsive response state ($F_{1,59}$=13.9, p=0.0004).

Figure 6:
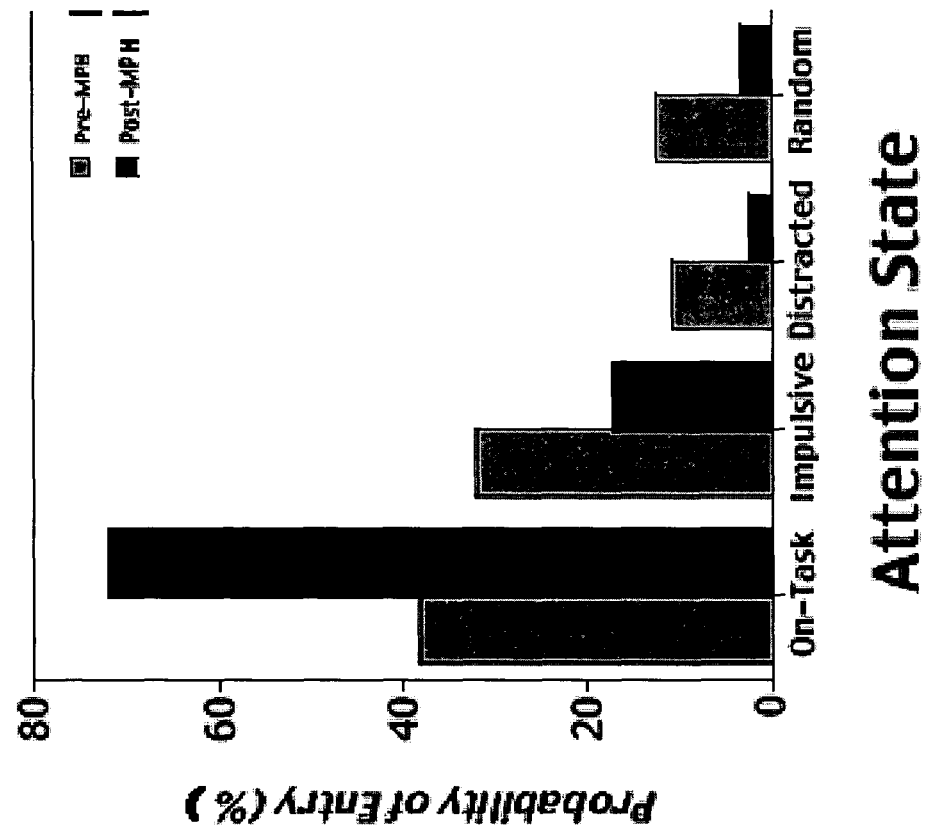
FIG. 6 is a graph showing the probability of subjects with ADHD entering a specific attentional performance state from another state prior to and following probe-dose treatment with methylphenidate.

FIG. 6 shows that MPH also reduced the likelihood that a child with ADHD would enter any inattentive state from another state. Thus, MPH reduced by 84% ($F_{1,59}$=31.34, $p<10^{-6}$), 31% ($F_{1,59}$=21.97, p=0.00002) and 84% ($F_{1,59}$=8.77, p=0.004) respectively, the probability that an ADHD child would enter a distracted, impulsive or random response state. Conversely, MPH increased by 114% the probability that an ADHD child would enter into an attentive on-task state from another state ($F_{1,49}$=51.33, $p<10^{-8}$).

Interrelationship of CPT Measures

Although errors of commission have often been used as an index of impulsivity, and errors of omission as an estimate of distraction (e.g., Halperin, Int. J. Neurosci. 58:171-182, 1991; Trommer et al., Ann. Neurol. 24:610-614, 1988), there was a highly significant correlation between omission errors and commission errors (r=0.722, n=60, $p<10^{-11}$), indicating that they do not provide independent information about attention state. In contrast, there was no significant association between percent time spent in impulsive or distracted states (r=−0.02, n=60, p>0.8), impulsive or random states (r=0.09, n=60, p>0.4), and random or distracted states (r=−0.03, n=60, p>0.7). Principal component analysis with varimax rotation (SYSTAT) indicates that impulsive, distracted and random response state measures load onto impulsive, distracted and random response factors with weights of 0.999, respectively, and load on to each of the other factor with weights less than 0.05. In short, they appear to provide distinctly different types of information about CPT performance.

Percent time spent in impulsive state and random state correlated to a moderate degree with errors of commission and errors of omission (impulsive state: multiple regression r=0.539, $F_{2,65}$=13.1, p<0.00002; random state: multiple r=0.476, $F_{2,65}$=9.39, p<0.0003). This suggests that about 23-29% of the variance in these attention performance state measures could be explained by a composite of commission and omission errors. Percent time in the distracted state did not correlate significantly with either errors of omission or errors of commission or their multiple regression composite (multiple r=0.181, $F_{2,65}$=1.09, p>0.3). Hence, it seems that only about 3% of the variance in the measure of percent time distracted could be inferred from overall measures of commission and omission errors.

There were also no significant correlations between the subject's degree of improvement due to MPH in these inattentive states. Degree of reduction in impulsive performance (for those subjects who had impulsive errors) failed to correlate with their degree of reduction in distracted performance (r=0.101, n=44, p>0.5), or random performance (r=0.088, n=37, p>0.6). Degree of reduction in distracted performance was also uncorrelated with reduction in random performance (r=0.223, n=30, p>0.2). In contrast, there was a significant association between degree of reduction in omission errors and degree of reduction in commission errors (r=0.318, n=59, p<0.02).

Relationship Between Inattention and Hyperactivity

Degree of fidgeting during the test was quantified using infrared motion analysis. Correlation analysis was used to ascertain the degree of association between each child's level of hyperactivity and the percent time they spent in impulsive, distracted and random attention response states. There was a significant correlation between the number of microevents and the percent time spent distracted (r=0.446, n=60, p=0.0004). A 10% increment in percent time distracted was associated with an increase of 3.6 meters in head movement displacement during the 15-minute test. There were no significant correlations between activity and impulsivity (r=0.066, n=60, p>0.6) or between activity and random responding (r=0.017, n=60, p>0.8). There were significant correlations between activity and errors of omission (r=0.343, n=60, p<0.008), and between activity and variability (standard deviation) in response latency (r=0.304, n=60, p<0.02). There were no significant correlations between activity and errors of commission (r=0.172, n=60, p=0.2), or between activity and mean response latency (r=0.176, n=60, p=0.2).

Subtyping by Attention States

As seen in FIG. 4, there were several differing patterns of shifting attention performance on the CPT. Some children were on-task throughout the test, while others had either a predominantly random, impulsive, or distracted pattern. To further explore these differences we classified children into one of five performance patterns. Classification was initially made through cluster analysis (SYSTAT), which used an iterative assignment algorithm to constitute different clusters of subjects that maximized the multivariate (MANOVA) statistical difference between clusters based on the percent of epochs spent on-task, distracted, impulsive or randomly responding. A five-cluster configuration appeared to provide a very robust statistical solution (MANOVA $p<10^{-15}$), and identified clusters of subjects who were "predominantly, on-task", "predominantly distracted", "predominantly-impulsive", "predominantly-random" or "mixed". Since cluster memberships were based on distances calculated in multidimensional space and had no direct meaning, we delineated 5 subtypes with easily defined membership criteria that closely approximated the cluster arrangement. Children were defined as "predominantly on-task" if they spent more than 75% of their time on-task, and had no "random" performance (n=10). Conversely, children who were "predominantly random" spent more time in a random performance state (35-100%) than in any other inattentional state, and spent very little time on-task (n=7). Children who were "predominantly impulsive" spent more time in an impulsive state than any other inattentional state, and spent at least 75% more time impulsive than distracted or random (n=23). Children who were "predominantly distracted" spent more time in a distracted state that in any other inattentional state, and spent at least 60% more time distracted than impulsive or purely random (n=5). The remaining children were classified as "mixed" because they either had similar ratios of impulsive-to-distracted, or impulsive-to-random behaviors (n=15). Multivariate differences between subtypes were extremely high (Wilks' lambda=0.026, $F_{16,159}$=22.82, $p<10^{-15}$).

There were significant differences between these subtypes in number of microevents ($F_{4,55}$=3.21, p<0.02) and displacement ($F_{4,55}$=3.10, p<0.02). Off medication, children with the "predominantly distracted" response pattern were significantly more active than children with "predominantly impulsive" and "predominantly on-task" response patterns (Tukey test, p<0.02, p<0.03, respectively; see Table III). All of these groups were significantly more active than controls who moved on average only 1846±1493 microevents per 5 minute period and covered in that time a distance of only 2.46±3.57 meters. MPH attenuated the activity of ADHD children across all groups ($F_{1,55}$=65.60, $p<10^{-10}$), though children who were "predominantly distracted" remained more active than children who were "predominantly impulsive" (Tukey test, p=0.02).

TABLE III

Effect of MPH on Performance of Children with Different Attention State Subtypes

| MEASURES | Predominantly On-Task | Predominantly Distracted | Predominantly Impulsive | Predominantly Random | Mixed Patterns |
|---|---|---|---|---|---|
| N | 10 | 5 | 23 | 7 | 15 |
| Off Medication | | | | | |
| % On-Task | 85 ± 7 | 37 ± 21 | 50 ± 19 | 3 ± 5 | 23 ± 23 |
| % Impulsive | 12 ± 7 | 16 ± 10 | 40 ± 16 | 25 ± 16 | 45 ± 15 |
| % Distracted | 3 ± 4 | 44 ± 14 | 6 ± 6 | 7 ± 9 | 16 ± 8 |
| % Random+ | 0 ± 0 | 4 ± 8 | 4 ± 4 | 65 ± 22 | 17 ± 10 |
| Fluctuations | 7.2 ± 3.3 | 13.0 ± 4.2 | 13.0 ± 3.4 | 13.3 ± 4.2 | 15.0 ± 3.2 |
| % Commisions | 15 ± 14 | 12 ± 5 | 25 ± 15 | 40 ± 25 | 41 ± 20 |
| % Omissions | 6 ± 4 | 9 ± 5 | 11 ± 17 | 26 ± 17 | 17 ± 13 |
| Latency | 551 ± 83 | 575 ± 61 | 518 ± 76 | 518 ± 74 | 554 ± 77 |
| Response S.D. | 162 ± 31 | 170 ± 35 | 155 ± 52 | 229 ± 78 | 208 ± 56 |
| Microevents | 2353 ± 1494 | 4814 ± 2854 | 2403 ± 1363 | 2623 ± 739 | 3138 ± 1264 |
| Displacement (m) | 4.01 ± 3.14 | 10.19 ± 8.11 | 4.32 ± 3.22 | 4.74 ± 1.43 | 6.01 ± 3.28 |
| Methylphenidate | | | | | |
| % On-Task | 89 ± 15 | 79 ± 18** | 83 ± 21†† | 45 ± 38* | 67 ± 24†† |
| % Impulsive | 10 ± 13 | 15 ± 15 | 14 ± 15†† | 27 ± 16 | 27 ± 19* |
| % Distracted | 1 ± 2* | 6 ± 6† | 2 ± 4† | 4 ± 3 | 2 ± 5†† |
| % Random+ | 0 ± 1 | 0 ± 0 | 1 ± 4** | 24 ± 36* | 3 ± 9† |
| Fluctuations | 4.4 ± 5.1 | 7.4 ± 5.2 | 5.8 ± 5.7†† | 9.8 ± 3.4 | 9.1 ± 5.4†† |
| % Commisions | 12 ± 11 | 5 ± 3* | 13 ± 17†† | 18 ± 27* | 17 ± 13†† |
| % Omissions | 1 ± 2** | 2 ± 1* | 6 ± 17†† | 6 ± 10* | 8 ± 20 |
| Latency | 514 ± 65* | 545 ± 77 | 486 ± 58†† | 507 ± 98 | 496 ± 71** |
| Response S.D. | 131 ± 34† | 124 ± 35 | 115 ± 71†† | 142 ± 33* | 122 ± 27†† |
| Microevents | 1044 ± 899†† | 1966 ± 990 | 650 ± 419†† | 1496 ± 826** | 1267 ± 1197†† |
| Displacement (m) | 1.64 ± 1.68† | 2.83 ± 1.62 | 0.97 ± 0.68†† | 2.20 ± 1.28† | 2.01 ± 2.16†† |

Baseline vs. MPH,
*p < 0.05,
**p < 0.01,
†p < 0.005,
††p < 0.001

There were significant differences between these subtypes in the number of state shifts made during the CPT test ($F_{4,55}=9.05$, $p<10^{-5}$). Off medication, children in the "predominantly on-task" group had fewer state shifts than children in any other subgroup (Tukey test, all p values<0.01). This however, was largely a consequence of the "predominantly on-task" group spending more time in their predominant state (85% of their time on average) than children in any of the other groups spent in their predominant state (54-60% of their time on average). Adjusting the number of state shifts by time spent in the predominant state eliminated any difference between the 'predominantly ontask' group (11.8 shifts) and any of the other groups in frequency of state shifts (12.1-14.0 shifts). Interestingly, normal controls spent the same amount of time in the on-task state as children in the 'predominantly on-task group'. However, normal controls had fewer shifts that ADHD subjects even after the data were corrected for time spent in the predominant state ($F_{1,65}=6.89$, $p<0.01$). This suggest that normal controls have fewer shifts than the ADHD subjects both because of the large amount of time spent in the 'on-task' state, and because of a lower rate of shifting between epochs not spent in the 'ontask' state.

MPH attenuated the number of state shifts across all groups ($F_{1,55}=43.50$, $p<10^{-7}$), and differences between the groups fell short of significant ($F_{4,55}=2.05$, $p=0.10$). On MPH, there were still notable group differences in on-task responding ($F_{4,55}=4.93$, $p<0.002$) which remained significantly worse in subjects who were "predominantly random" than those who were classified as "predominantly impulsive" or "predominantly on-task" (Tukey test, both p<0.005). There were also persistent group differences in random responding (F4, 55=4.89, p<0.002), which remained significantly higher in subjects who were classified as "predominantly random" responders than in any other group (Tukey test, all p values<0.02).

However, even without treatment there were relatively few differences between these subgroups on traditional CPT measures. Errors of omission ($F_{4,55}=4.89$, $p<0.002$) were higher in "predominantly random" responders than in subjects who were "predominantly on-task" (Tukey test, p<0.05). Errors of commission ($F_{4,55}=5.73$, $p<0.001$) were higher in "predominantly random" and "mixed pattern" responders than in children who were "predominantly distracted" (Tukey test, p=0.06, p<0.02, respectively), or "predominantly on-task" (Tukey test, p<0.05, p<0.005, respectively). Subjects with "predominantly impulsive" response patterns also had a lower degree of variability (S.D.) in response latency ($F_{4,55}=4.14$, $p=0.005$), than subjects with a "predominantly random" or "mixed pattern" (Tukey test, all p values<0.04). There were no differences between the subgroups in correct response latency ($F_{4,55}=1.05$ p>0.3). None of the subgroup differences on the traditional CPT measures persisted when subjects received probe-dose MPH.

Discussion

A novel dynamic temporal strategy for the analysis of CPT data showed that boys with ADHD had many more shifts in attention performance and spent much less time in an on-task attention state than normal controls. On average, ADHD boys spent 33% of their time in an impulsive state in which they were attentive to the presence or absence of stimuli, but either insufficiently attentive to the difference between targets and nontargets or unable to effectively inhibit their response to non-targets. They spent approximately 11% of their time in a distracted state in which they were partially attentive to the task, performing significantly better than chance, but they missed a significant number of targets. They also spent approximately 12% of their time in a random response state in which they ceased to be attentive to the task and responded at a level no better than chance. These appear to be distinct states or orthogonal measures of CPT performance as the percent time spent in any one state was uncorrelated with percent time spent in any other state. This means that time spent in any one inattentive performance state seems to provide no information about time spent in another inattentive state. In contrast, errors of omission and errors of commission are highly correlated, suggesting that they do not provide independent information about attention, even though traditionally CPT errors of commission have been used as an index of impulsivity and errors of omission an index of distraction (e.g., (Trommer et al., 1988. supra).

It should be emphasized that the complete lack of correlation between the impulsive, distracted and response states observed in the study was not merely a mathematical consequence of the state definitions. If response errors occurred randomly then very accurate subjects would spend virtually no time in the impulsive, distracted and random states, fairly accurate subjects would spend a modest amount of time in these states, and inaccurate subjects would spend a considerable amount of time in these states. Hence, percent time in these states would correlate significantly across subjects if errors occurred at random. This was born out by a Monte-Carlo simulation in which we modeled performance of 100 subjects who varied in accuracy from 60% to 100%, who had a 2-fold greater proclivity toward errors of commission than errors of omission, and who made errors at random based on their accuracy rate. Under these circumstances there were substantial correlations between distracted and impulsive periods ($r=0.492$, $n=100$, $p<10-6$) and distracted and random periods ($r=0.414$, $p<0,00002$). Lack of correlation in the actual population occurred not by definition but because there were discrete subsets of subjects with much greater proclivity towards one type of impaired attention response state than another with corresponding non-random error distribution rates.

MPH markedly diminished the number of attention shifts and produced a 77% increase in percent time spent in a fully attentive on-task state. The distracted, impulsive, and random states of inattention were all highly responsive to treatment with MPH. However, MPH exerted a stronger effect on the distracted state than on the impulsive state. (e.g., 93% vs 42% reduction in the probability of persisting in the state).

ADHD children with "predominantly random" response profiles did not show a full restoration in CPT performance following probe dose treatment with MPH. It will be very interesting to ascertain whether other agents are more effective in normalizing their test performance. Studies are currently in progress to compare different agents to determine whether they exert similar effects on these different states of inattention, or if different drugs have unique profiles of actions.

We were surprised that level of activity during the attention task correlated only with his percent time spent in the distracted state, with no significant correlation between activity and impulsivity, or between activity and random responding. This finding was supported by the observation of a significant association between activity level and errors of omission but not between activity level and errors of commission. A priori, we had predicted that there would be a significant association between their level of activity and percent time spent in an impulsive state, as DSM-IV (APA, Diagnostic and Statistical Manual of Mental Disorders, $4^{th}$ ed. Washington, D.C., American Psychiatric Assoc., 1994) links hyperactivity with impulsivity. However, the hyperactive-impulsive link may be more of a conceptual than empirical association. The National Field Trial of DSM-III-R criteria for Disruptive Behavioral Disorders listed the symptoms of ADHD in order of their discriminant validity (Spitzer et al., J. Am. Acad. Child Adolesc. Psychiatry 29:690-697, 1990). This trial identified "fidgeting with hands or feet or squirming in the seat" as the most discriminating feature of ADHD. "Difficulty remaining seated" was the second most discriminative feature, and being "easily distracted by extraneous stimuli" was the third most discriminative symptom of this disorder (Spitzer et al., 1990, supra). Hence, fidgetiness and distractibility may be closely connected fundamental core components of this disorder.

Attention is generally regarded as an input process involving focusing, and selection in which sensory or mental stimuli are brought to the forefront of awareness (Barkley, Psychological Bulletin 121:65-94, 1997). This capacity is compromised to some extent during the distracted states, as there is diminished awareness of the relevant stimuli. In contrast, we would argue that the impulsive and random response states more likely reflect problems with performance than attention. In the random response state, the individual has disengaged from the task and the device is recording their lack of engagement rather than their attention capacity. In the impulsive state, the individual is highly attentive to the presentation of stimuli, and is often eagerly engaged in the task. Their occasional commission errors appear to reflect a diminished capacity to inhibit rapid responses more than an attention problem, as their errors are often accompanied by verbal exclamations of frustration. Our findings thus suggest that children with ADHD are most fidgety during those periods in which they are partially attentive and partially distracted, and that they are less hyperactive during periods when they are either entirely disengaged in the task, or highly engaged but responding impulsively.

Analysis of these attention performance states may reveal different properties of therapeutic drugs. One property may be the capacity to diminish overly enthusiastic responses, which would be reflected in the pattern of impulsive performance. Another capacity may be an enhanced ability to tolerate boredom or monotony, which would be reflected in a reduction in random performance. A third capacity may be greater freedom from distraction, which is reflected in improvement in the distracted performance component. It is interesting that there were no significant correlations between degree of improvement in one performance component (distracted, impulsive or random) and any other. Hence, the beneficial effects of medications on these performance states may stem from actions on multiple brain regions or transmitter systems.

Children with ADHD differed from one another in their propensity to manifest different types of attention performance problems on the CPT test. Children who were "predominantly distracted" were the most active both on and off medication. Children who were "predominantly random" off medication continued to manifest more problems with attention task performance following probe dose MPH, though their capacity to sit still normalized. Further research is needed to ascertain whether these CPT defined attentional subtypes are stable and have any value in our understanding of ADHD as a heterogeneous disorder.

The decision to categorize behavior into on-task, distracted, impulsive and random performance, and the specific state criteria selected were based on logic, reason, and probability considerations. The results obtained using these criteria provided a more robust discrimination between ADHD subjects and controls than traditional CPT measures, and were more strongly influenced by medication. The inattentive performance state measures were also distinct and uncorrelated. This suggests that the selected criteria have value and convey unique information about attentional processes.

Attention can shift very rapidly from distracted to on-task state, and it is possible that children can shift into and out of impulsive and random response states more rapidly than we could detect with a 30-second assessment window. We selected a 30-second sample window to provide enough stimuli with which to classify attentional performance with reasonably high accuracy. During each 30-second interval, the child is exposed to 15 stimuli, each of which has a 50% probability of being a target. Children who are randomly responding may in the course of 30 seconds respond to all stimuli, fail to respond to any stimuli, or respond to some intermediate percentage. Obviously, by chance there is a certain probability that random responses could appear accurate. Specifically, with this number of targets and this type of variable response rate there is a 0.077%, 3.557% and 8.512% chance that random responses could appear to be on-task, impulsive, or distracted, respectively. Hence, the 30-second response window represents a compromise between the need to rapidly assess performance states and the need to make these determinations with an acceptably high degree of accuracy. Greater accuracy could be obtained by selection of a large sampling interval at the expense of temporal resolution.

The main purpose of the paper was to ascertain the effects of methylphenidate on attentional performance of children with ADHD, and for these comparisons we had a large sample size and a high degree of statistical power. There were only 5 ADHD children out of 60 who met the criteria for the "predominantly distracted" subtype or cluster. While the differences between the "predominantly impulsive", "predominantly random", and "predominantly distracted" subtypes were interesting, these differences will require replication and more detailed evaluation in larger studies.

Overall, this study shows that parceling the CPT task into brief increments, and assessing the nature of CPT performance during each increment, has great value in the assessment of children with ADHD and in evaluation of drug response. Unlike conventional analysis of omission and commission rates, which are highly correlated, measures of time spent in a distracted state, impulsive state, and random response state are uncorrelated. Further, the number of state fluctuations and percent time spent on-task are very robust measures in which there is a greater effect size difference between ADHD and healthy control children. This new means of analysis should enhance the value of CPT tests in research on drug effects, and research correlating attentional performance ith brain function. These new analyses may also enhance the clinical utility of the CPT test as a means for titrating response to medication in a controlled laboratory setting.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each individual publication was specifically and individually indicated to be incorporated by reference.

What is claimed is:

1. A method for diagnosing a psychological, neurological, or behavioral disorder in a subject, said method comprising:
   (a) providing from said subject scoring data that has been collected by (i) presenting to said subject a sequence comprising target and nontarget stimuli during a continuous testing period; and (ii) scoring the response of said subject on the number of targets responded to and the number of nontargets responded to;

(b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in an impulsive attentional state, and (iv) calculating the amount of time said subject is in an impulsive attentional state during said continuous testing period; and (c) on the basis of the results of step (b), diagnosing said subject.

2. A method for diagnosing a psychological, neurological, or behavioral disorder in a subject, said method comprising:

(a) presenting to said subject a sequence comprising target and nontarget stimuli during a continuous testing period, recording the responses of said subject to produce subject data, and transmitting said subject data to a computer for analysis;

(b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in an impulsive attentional state, and (b4) calculating the amount of time said subject is in an impulsive attentional state during said continuous testing period; and (c) on the basis of the analysis of step (b), diagnosing said subject.

3. The method of claim 1 or 2, wherein said stimuli are visual symbols selected from numbers, letters, shapes, or a combination thereof.

4. The method of claim 1 or 2, wherein said stimuli are auditory.

5. The method of claim 1 or 2, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

6. The method of claim 5, wherein said disorder is attention deficit hyperactivity disorder.

7. The method of claim 1 or 2, wherein step (c) further comprises comparing the results of step (b) in subjects diagnosed with a disorder and subjects not diagnosed with said disorder.

8. The method of claim 1 or 2, wherein said subject is involved in a clinical trial of a therapy for a psychological, neurological, or behavioral disorder.

9. The method of claim 1 or 2, wherein said stimuli are presented using a computer screen or speaker and each subject's responses are stored in a computer.

10. The method of claim 1 or 2, wherein said subject communicates with a test administrator across a network.

11. The method of claim 1 or 2, wherein the number of stimuli is 15 or greater.

12. The method of claim 1 or 2, wherein each of said epochs are the same length.

13. A method for diagnosing a psychological, neurological, or behavioral disorder in a subject, said method comprising:

(a) providing from said subject scoring data that has been collected by (i) presenting to said subject a sequence comprising target and nontarget stimuli during a continuous testing period; and (ii) scoring the response of said subject on the number of targets responded to and the number of nontargets responded to;

(b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in a distracted attentional state, and (iv) calculating the amount of time said subject is in a distracted attentional state during said continuous testing period; and (c) on the basis of the results of step (b), diagnosing said subject.

14. A method for diagnosing a psychological, neurological, or behavioral disorder in a subject, said method comprising:

(a) presenting to said subject a sequence comprising target and nontarget stimuli during a continuous testing period, recording the responses of said subject to produce subject data, and transmitting said subject data to a computer for analysis;

(b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in a distracted attentional state, and (b4) calculating the amount of time said subject is in a distracted attentional state during said continuous testing period; and (c) on the basis of the analysis of step (b), diagnosing said subject.

15. The method of claim 13 or 14, wherein said stimuli are visual symbols selected from numbers, letters, shapes, or a combination thereof.

16. The method of claim 13 or 14, wherein said stimuli are auditory.

17. The method of claim 13 or 14, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

18. The method of claim 17, wherein said disorder is attention deficit hyperactivity disorder.

19. The method of claim 13 or 14, wherein step (c) further comprises comparing the results of step (b) in subjects diagnosed with a disorder and subjects not diagnosed with said disorder.

20. The method of claim 13 or 14, wherein said subject is involved in a clinical trial of a therapy for a psychological, neurological, or behavioral disorder.

21. The method of claim 13 or 14, wherein said stimuli are presented using a computer screen or speaker and each subject's responses are stored in a computer.

22. The method of claim 13 or 14, wherein said subject communicates with a test administrator across a network.

23. The method of claim 13 or 14, wherein the number of stimuli is 15 or greater.

24. The method of claim 13 or 14, wherein each of said epochs are the same length.

25. A method for diagnosing a psychological, neurological, or behavioral disorder in a subject, said method comprising:
   (a) providing from said subject scoring data that has been collected by (i) presenting to said subject a sequence comprising target and nontarget stimuli during a continuous testing period; and (ii) scoring the response of said subject on the number of targets responded to and the number of nontargets responded to;
   (b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in an on-task attentional state, and (iv) calculating the amount of time said subject is in an on-task attentional state during said continuous testing period; and
   (c) on the basis of the results of step (b), diagnosing said subject.

26. A method for diagnosing a psychological, neurological, or behavioral disorder in a subject, said method comprising:
   (a) presenting to said subject a sequence comprising target and nontarget stimuli during a continuous testing period, recording the responses of said subject to produce subject data, and transmitting said subject data to a computer for analysis;
   (b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in an on-task attentional state, and (b4) calculating the amount of time said subject is in an on-task attentional state during said continuous testing period; and
   (c) on the basis of the analysis of step (b), diagnosing said subject.

27. The method of claim 25 or 26, wherein said stimuli are visual symbols selected from numbers, letters, shapes, or a combination thereof.

28. The method of claim 25 or 26, wherein said stimuli are auditory.

29. The method of claim 25 or 26, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

30. The method of claim 29, wherein said disorder is attention deficit hyperactivity disorder.

31. The method of claim 25 or 26, wherein step (c) further comprises comparing the results of step (b) in subjects diagnosed with a disorder and subjects not diagnosed with said disorder.

32. The method of claim 25 or 26, wherein said subject is involved in a clinical trial of a therapy for a psychological, neurological, or behavioral disorder.

33. The method of claim 25 or 26, wherein said stimuli are presented using a computer screen or speaker and each subject's responses are stored in a computer.

34. The method of claim 25 or 26, wherein said subject communicates with a test administrator across a network.

35. The method of claim 25 or 26, wherein the number of stimuli is 15 or greater.

36. The method of claim 25 or 26, wherein each of said epochs are the same length.

37. A method for diagnosing a psychological, neurological, or behavioral disorder in a subject, said method comprising:
   (a) providing from said subject scoring data that has been collected by (i) presenting to said subject a sequence comprising target and nontarget stimuli during a continuous testing period; and (ii) scoring the response of said subject on the number of targets responded to and the number of nontargets responded to;
   (b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in a randomly responding attentional state, and (iv) calculating the amount of time said subject is in a randomly responding attentional state during said continuous testing period; and
   (c) on the basis of the results of step (b), diagnosing said subject.

38. A method for diagnosing a psychological, neurological, or behavioral disorder in a subject, said method comprising:
   (a) presenting to said subject a sequence comprising target and nontarget stimuli during a continuous testing period, recording the responses of said subject to produce subject data, and transmitting said subject data to a computer for analysis;
   (b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in a randomly responding attentional state, and (b4) calculating the amount of time said subject is in a randomly responding attentional state during said continuous testing period; and
   (c) on the basis of the analysis of step (b), diagnosing said subject.

39. The method of claim 37 or 38, wherein said stimuli are visual symbols selected from numbers, letters, shapes, or a combination thereof.

40. The method of claim 37 or 38, wherein said stimuli are auditory.

41. The method of claim 37 or 38, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

42. The method of claim 41, wherein said disorder is attention deficit hyperactivity disorder.

43. The method of claim 37 or 38, wherein step (c) further comprises comparing the results of step (b) in subjects diagnosed with a disorder and subjects not diagnosed with said disorder.

44. The method of claim 37 or 38, wherein said subject is involved in a clinical trial of a therapy for a psychological, neurological, or behavioral disorder.

45. The method of claim 37 or 38, wherein said stimuli are presented using a computer screen or speaker and each subject's responses are stored in a computer.

46. The method of claim 37 or 38, wherein said subject communicates with a test administrator across a network.

47. The method of claim 37 or 38, wherein the number of stimuli is 15 or greater.

48. The method of claim 37 or 38, wherein each of said epochs are the same length.

49. A method for determining the efficacy of a therapy for a subject, said method comprising:
(a) providing from said subject scoring data that has been collected by (i) presenting to said subject a sequence comprising target and nontarget stimuli during a continuous testing period; and (ii) scoring the response of said subject on the number of targets responded to and the number of nontargets responded to;
(b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in an impulsive attentional state, and (iv) calculating the amount of time said subject is in an impulsive attentional state during said continuous testing period;
(c) providing control data produced by performing steps (a) and (b) on either said subject when not undergoing treatment with said therapy or on a control subject not undergoing treatment with said therapy; and
(d) comparing the results of steps (b) to the control data of step (c) to determine the effect of said therapy on said subject.

50. A method for determining the efficacy of a therapy for a subject, said method comprising:
(a) presenting to said subject a sequence comprising target and nontarget stimuli during a continuous testing period, recording the responses of said subject to produce subject data, and transmitting said subject data to a computer for analysis;
(b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in an impulsive attentional state, and (b4) calculating the amount of time said subject is in an impulsive attentional state during said continuous testing period;
(c) providing control data produced by performing steps (a) and (b) on either said subject when not undergoing treatment with said therapy or on a control subject not undergoing treatment with said therapy; and
(d) on the basis of a comparison of the results of step (b) to the control data of step (c), determining the effect of said therapy on said subject.

51. The method of claim 49 or 50, wherein said stimuli are visual symbols selected from numbers, letters, shapes, or a combination thereof.

52. The method of claim 49 or 50, wherein said stimuli are auditory.

53. The method of claim 49 or 50, wherein said subject is diagnosed with a psychological, neurological, or behavioral disorder.

54. The method of claim 53, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

55. The method of claim 54, wherein said disorder is attention deficit hyperactivity disorder.

56. The method of claim 49 or 50, wherein said subject is involved in a clinical trial of a therapy for a psychological, neurological, or behavioral disorder.

57. The method of claim 49 or 50, wherein said method is used to determine the preferred therapy for the treatment of a psychological, neurological, or behavioral disorder.

58. The method of claim 49 or 50, wherein said stimuli are presented using a computer screen or speaker and each subject's responses are stored in a computer.

59. The method of claim 49 or 50, wherein said subject communicates with a test administrator across a network.

60. The method of claim 49 or 50, wherein the number of stimuli is 15 or greater.

61. The method of claim 49 or 50, wherein each of said epochs are the same length.

62. A method for determining the efficacy of a therapy for a subject, said method comprising:
(a) providing from said subject scoring data that has been collected by (i) presenting to said subject a sequence comprising target and nontarget stimuli during a continuous testing period; and (ii) scoring the response of said subject on the number of targets responded to and the number of nontargets responded to;
(b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in a distracted attentional state, and (iv) calculating the amount of time said subject is in a distracted attentional state during said continuous testing period;
(c) providing control data produced by performing steps (a) and (b) on either said subject when not undergoing treatment with said therapy or on a control subject not undergoing treatment with said therapy; and
(d) comparing the results of steps (b) to the control data of step (c) to determine the effect of said therapy on said subject.

63. A method for determining the efficacy of a therapy for a subject, said method comprising:
(a) presenting to said subject a sequence comprising target and nontarget stimuli during a continuous testing period, recording the responses of said subject to produce subject data, and transmitting said subject data to a computer for analysis;
(b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in a distracted attentional state, and (b4) calculating the amount of time said subject is in a distracted attentional state during said continuous testing period;
- (c) providing control data produced by performing steps (a) and (b) on either said subject when not undergoing treatment with said therapy or on a control subject not undergoing treatment with said therapy; and
- (d) on the basis of a comparison of the results of step (b) to the control data of step (c), determining the effect of said therapy on said subject.

64. The method of claim 62 or 63, wherein said stimuli are visual symbols selected from numbers, letters, shapes, or a combination thereof.

65. The method of claim 62 or 63, wherein said stimuli are auditory.

66. The method of claim 62 or 63, wherein said subject is diagnosed with a psychological, neurological, or behavioral disorder.

67. The method of claim 66, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

68. The method of claim 67, wherein said disorder is attention deficit hyperactivity disorder.

69. The method of claim 62 or 63, wherein said subject is involved in a clinical trial of a therapy for a psychological, neurological, or behavioral disorder.

70. The method of claim 62 or 63, wherein said method is used to determine the preferred therapy for the treatment of a psychological, neurological, or behavioral disorder.

71. The method of claim 62 or 63, wherein said stimuli are presented using a computer screen or speaker and each subject's responses are stored in a computer.

72. The method of claim 62 or 63, wherein said subject communicates with a test administrator across a network.

73. The method of claim 62 or 63, wherein the number of stimuli is 15 or greater.

74. The method of claim 62 or 63, wherein each of said epochs are the same length.

75. A method for determining the efficacy of a therapy for a subject, said method comprising:
- (a) providing from said subject scoring data that has been collected by (i) presenting to said subject a sequence comprising target and nontarget stimuli during a continuous testing period; and (ii) scoring the response of said subject on the number of targets responded to and the number of nontargets responded to;
- (b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in an on-task attentional state, and (iv) calculating the amount of time said subject is in an on-task attentional state during said continuous testing period;
- (c) providing control data produced by performing steps (a) and (b) on either said subject when not undergoing treatment with said therapy or on a control subject not undergoing treatment with said therapy; and
- (d) comparing the results of steps (b) to the control data of step (c) to determine the effect of said therapy on said subject.

76. A method for determining the efficacy of a therapy for a subject, said method comprising:
- (a) presenting to said subject a sequence comprising target and nontarget stimuli during a continuous testing period, recording the responses of said subject to produce subject data, and transmitting said subject data to a computer for analysis;
- (b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in an on-task attentional state, and (b4) calculating the amount of time said subject is in an on-task attentional state during said continuous testing period;
- (c) providing control data produced by performing steps (a) and (b) on either said subject when not undergoing treatment with said therapy or on a control subject not undergoing treatment with said therapy; and
- (d) on the basis of a comparison of the results of step (b) to the control data of step (c), determining the effect of said therapy on said subject.

77. The method of claim 75 or 76, wherein said stimuli are visual symbols selected from numbers, letters, shapes, or a combination thereof.

78. The method of claim 75 or 76, wherein said stimuli are auditory.

79. The method of claim 75 or 76, wherein said subject is diagnosed with a psychological, neurological, or behavioral disorder.

80. The method of claim 79, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

81. The method of claim 80, wherein said disorder is attention deficit hyperactivity disorder.

82. The method of claim 75 or 76, wherein said subject is involved in a clinical trial of a therapy for a psychological, neurological, or behavioral disorder.

83. The method of claim 75 or 76, wherein said method is used to determine the preferred therapy for the treatment of a psychological, neurological, or behavioral disorder.

84. The method of claim 75 or 76, wherein said stimuli are presented using a computer screen or speaker and each subject's responses are stored in a computer.

85. The method of claim 75 or 76, wherein said subject communicates with a test administrator across a network.

86. The method of claim 75 or 76, wherein the number of stimuli is 15 or greater.

87. The method of claim 75 or 76, wherein each of said epochs are the same length.

88. A method for determining the efficacy of a therapy for a subject, said method comprising:

(a) providing from said subject scoring data that has been collected by (i) presenting to said subject a sequence comprising target and nontarget stimuli during a continuous testing period; and (ii) scoring the response of said subject on the number of targets responded to and the number of nontargets responded to;

(b) on the basis of said scoring data, (i) dividing said sequence into three or more epochs and classifying the attentional state of said subject during each epoch, (ii) calculating the number of shifts in the attentional state of said subject during said continuous testing period, (iii) identifying epochs in which said subject is in a randomly responding attentional state, and (iv) calculating the amount of time said subject is in a randomly responding attentional state during said continuous testing period;

(c) providing control data produced by performing steps (a) and (b) on either said subject when not undergoing treatment with said therapy or on a control subject not undergoing treatment with said therapy; and (d) comparing the results of steps (b) to the control data of step (c) to determine the effect of said therapy on said subject.

89. A method for determining the efficacy of a therapy for a subject, said method comprising:

(a) presenting to said subject a sequence comprising target and nontarget stimuli during a continuous testing period, recording the responses of said subject to produce subject data, and transmitting said subject data to a computer for analysis;

(b) receiving the results of said analysis, wherein said analysis comprises (i) scoring the response of said subject on the number of targets responded to and the number of nontargets responded to; and (ii) on the basis of said scoring data, (b1) dividing said sequence into three or more epochs and classifying the attentional state of said subject during each epoch, (b2) calculating the number of shifts in the attentional state of said subject during said continuous testing period, (b3) identifying epochs in which said subject is in a randomly responding attentional state, and (b4) calculating the amount of time said subject is in a randomly responding attentional state during said continuous testing period;

(c) providing control data produced by performing steps (a) and (b) on either said subject when not undergoing treatment with said therapy or on a control subject not undergoing treatment with said therapy; and (d) on the basis of a comparison of the results of step (b) to the control data of step (c), determining the effect of said therapy on said subject.

90. The method of claim 88 or 89, wherein said stimuli are visual symbols selected from numbers, letters, shapes, or a combination thereof.

91. The method of claim 88 or 89, wherein said stimuli are auditory.

92. The method of claim 88 or 89, wherein said subject is diagnosed with a psychological, neurological, or behavioral disorder.

93. The method of claim 92, wherein said disorder is depression, an anxiety disorder, schizophrenia, drug addiction, an eating disorder, attention deficit disorder, attention deficit hyperactivity disorder, a learning disorder, Alzheimer's disease, dementia, epilepsy, stroke, or traumatic brain injury.

94. The method of claim 93, wherein said disorder is attention deficit hyperactivity disorder.

95. The method of claim 88 or 89, wherein said subject is involved in a clinical trial of a therapy for a psychological, neurological, or behavioral disorder.

96. The method of claim 88 or 89, wherein said method is used to determine the preferred therapy for the treatment of a psychological, neurological, or behavioral disorder.

97. The method of claim 88 or 89, wherein said stimuli are presented using a computer screen or speaker and each subject's responses are stored in a computer.

98. The method of claim 88 or 89, wherein said subject communicates with a test administrator across a network.

99. The method of claim 88 or 89, wherein the number of stimuli is 15 or greater.

100. The method of claim 88 or 89, wherein each of said epochs are the same length.

\* \* \* \* \*

UNITED STATES PATENT AND TRADEMARK OFFICE
CERTIFICATE OF CORRECTION

| | | |
|---|---|---|
| PATENT NO. | : 7,942,828 B2 | Page 1 of 1 |
| APPLICATION NO. | : 10/771036 | |
| DATED | : May 17, 2011 | |
| INVENTOR(S) | : Teicher et al. | |

It is certified that error appears in the above-identified patent and that said Letters Patent is hereby corrected as shown below:

On the title page, item [56], under OTHER PUBLICATIONS, replace "Arve et al." with
--Asbjørnsen et al.--.

Column 1, Lines 56-57, replace "attention deficit and hyperactivity" with --and attention deficit hyperactivity--;

Line 57, replace "disorder." with --disorders.--.

Column 2, Line 17, replace "attention deficit and hyperactivity disorder" with
--attention deficit hyperactivity disorder--.

Column 3, Lines 26-27, replace "classifying response" with
--classifying a response--;

Line 37, replace "methyphenidate" with --methylphenidate--;

Line 39, replace "is proportion" with --is proportional--;

Line 51, replace "sate" with --state--;

Line 53, replace "implusivity" with --impulsivity--.

Column 4, Line 15, replace "calculated, and denoted T." with
--calculated and denoted T.--;

Line 15, replace "less than 25%, and the subject" with
--less than 25% and the subject--.

Signed and Sealed this
Thirteenth Day of November, 2012

David J. Kappos
*Director of the United States Patent and Trademark Office*

UNITED STATES PATENT AND TRADEMARK OFFICE
CERTIFICATE OF CORRECTION

PATENT NO.        : 7,942,828 B2
APPLICATION NO.   : 10/771036
DATED             : May 17, 2011
INVENTOR(S)       : Martin H. Teicher et al.

It is certified that error appears in the above-identified patent and that said Letters Patent is hereby corrected as shown below:

In the Specification

Column 4, Lines 33-34, replace "responding, is defined as" with --responding is defined as--.

Column 5, Line 5, replace "bloodstream" with --bloodstreams--;

Lines 16-17, "p<10-10" with --$p<10^{-10}$--;

Line 39, replace "states" with --state--;

Line 63-64, replace "Schedule for Affective Disorder and Schizophrenia for School-Age Children" with --Schedule for Affective Disorders and Schizophrenia for School-Age Children--;

Line 66, replace "have current" with --have a current--;

Lines 66-67, replace "a major" with --major--;

Line 67, replace "metal retardation" with --mental retardation--.

Column 6, Lines 25-26, replace "Schedule for Affective Disorder and Schizophrenia for School-Age Children" with --Schedule for Affective Disorders and Schizophrenia for School-Age Children--;

Line 40, replace "motionanalysis" with --motion analysis--;

Line 53, replace "1.0 mm, called microevents" with --1.0 mm called microevents--.

Column 7, Line 8, replace "response" with --a response--.

Signed and Sealed this
Eighteenth Day of March, 2014

Michelle K. Lee
*Deputy Director of the United States Patent and Trademark Office*

Column 8, Line 2, replace "medication, and had" with --medication and had--;

Line 10, replace "one of the alternative state" with --one of the alternative states--;

Line 21, replace "changes, and calculations" with --changes and calculations--;

Table 1, under Standard CPT Parameters, replace "Errors of Commision" with --Errors of Commission--.

Column 9, Line 1, replace "TABLE 2" with --TABLE II--;

Table 2, under Standard CPT Parameters, replace "Errors of Commision" with --Errors of Commission--;

Line 31, replace "due to marked" with --due to a marked--.

Column 10, Line 23, replace "p<10-11" with --$p<10^{-11}$--;

Line 33, replace "each of the other factor" with --each of the other factors--;

Line 39, replace "random'state:" with --random state:--.

Column 11, Line 29, replace "predominantlydistracted" with --predominantly distracted--.

Column 12, Line 6, replace "state, and spent" with --state and spent--;

Line 15-16, replace "impulsive-to-distracted, or" with --impulsive-to-distracted or--;

Table III, under Off Medication, replace "% Commisions" with --% Commissions--;

Table III, under Methylphenidate, replace "% Commisions" with --% Commissions--.

Column 13, Line 12, replace "ontask' group" with --on-task' group--;

Lines 16-17, replace "fewer shifts that ADHD subjects" with --fewer shifts than ADHD subjects--;

Lines 18-19, replace "This suggest" with --This suggests--;

Line 21, replace "state, and because" with --state and because--;

Line 22, replace "the 'ontask' state." with --the 'on-task' state.--;

Line 25, replace "fell short of significant" with --fell short of significance--;

CERTIFICATE OF CORRECTION (continued)
U.S. Pat. No. 7,942,828 B2

Lines 31-32, replace "F4,55=4.89" with -- $F_{4,55}$=4.89--;

Lines 34-35, replace "all p values<0.02" with --all p values < 0.02--;

Line 48, replace "p=0.005), than" with --p=0.005) than--.

Column 14, Line 12, replace "an index" with --as an index--;

Line 13, replace "supra)." with --supra)).--;

Line 28, replace "errors of omission, and who" with --errors of omission and who--;

Line 31, replace "p<10-6" with --$p<10^{-6}$--;

Line 32, replace "p<0,00002" with --p<0.00002--;

Line 43, replace "vs" with --vs.--;

Line 55, replace "with his percent time" with --with this percent time--;

Line 62, replace "between their level of activity" with --between the level of activity--.

Column 15, Line 14, replace "focusing, and selection" with --focusing and selection--;

Line 25, replace "stimuli, and is" with --stimuli and is--.

Column 16, Line 49, replace "ith" with --with--.